United States Patent [19]

Richardson et al.

[11] Patent Number: 4,542,645

[45] Date of Patent: Sep. 24, 1985

[54] APPARATUS AND METHODS FOR MEASURING MILK COAGULATION TIME AND RIGIDITY IN THE MANUFACTURE OF FERMENTED DAIRY PRODUCTS

[75] Inventors: Gary H. Richardson; J. Derle Thorpe, both of Logan, Utah

[73] Assignee: Utah State University Foundation, Logan, Utah

[21] Appl. No.: 528,732

[22] Filed: Sep. 1, 1983

[51] Int. Cl.[3] .................... G01N 11/16; G01N 33/04
[52] U.S. Cl. ........................................ 73/64.1; 73/169
[58] Field of Search ............................... 73/64.1, 169

[56] References Cited

U.S. PATENT DOCUMENTS

| | | | |
|---|---|---|---|
| 3,038,327 | 6/1962 | Resnick | 73/64.1 |
| 3,077,106 | 2/1963 | Fink | 73/64.1 |
| 4,437,337 | 3/1984 | Fenrick | 73/169 X |

FOREIGN PATENT DOCUMENTS

| | | | |
|---|---|---|---|
| 2227943 | 12/1973 | Fed. Rep. of Germany | 73/64.1 |
| 1219840 | 12/1959 | France | 73/169 |
| 120681 | 6/1958 | U.S.S.R. | 73/169 |
| 457011 | 2/1975 | U.S.S.R. | 73/64.1 |

OTHER PUBLICATIONS

Abstract 1621 from Chemistry and Physics for J. P. Ramet et al., "Considerations on the Mechanism of Milk Coagulation Using Pfizer Microbial Enzyme," Revue lait. fr. Industrie lait., 730–741, (1970).

Glazman, J., et al., *Low Molecular Weight Butyl Sealants Demonstrate Advantages of Using Gelation Timer*, In Adhesives Age, Apr. 1970, pp. 28–31.

Abstract 1622 from Chemistry and Physics for J. L. Edwards, Jr., "Bitterness and Proteolysis in Cheddar Cheese Made with Animal, Microbial, or Vegetable Rennet Enzymes," 30 Diss. Abstr. Int., Sect. B 4194, (1970).

"A New Instrument to Measure Cheese Curd Rigidity, and Preliminary Trials in Cheesemaking", 34 Journal of the Society of Dairy Technology, 139–142, No. 4 (Oct. 1981).

Abstract 3839 from Technology for J. C. Oosthuizen et al., "A Constant Speed, Fixed Angle Torsiometer for Measuring the Coagulation of Milk by Rennet," 9 S. Afr. J. Agric. Sci., 1011–1017, (1966).

G. H. Richardson et al., "Continuous Curd Tension Measurements During Milk Coagulation", 54 Journal of Dairy Science, 182–186 (1971).

Abstract 1192 from Chemistry and Physics for M. Eisele et al., "Effects of Certain Technological Treatments on the Rennet Coagulation of Milk", 15 Zesz. nauk. wyzsz. Szk. roln. Olsztyn., 463–472, (1963).

G. W. Scott Blair et al., "A Simple Method for Detecting an Early Stage in Coagulation of Rennetted Milk", 30 J. Dairy Res., 383–390 (1963).

Abstract 1193 from Chemistry and Physics for J. Budny et al., "Development of Objective Tests for Cheesemaking, I. Study of Milk Clot Firmness by Measurement of Visible Light Absorption," 21 Zesz. nauk. wyzsz. Szk. roln. Olsztyn., 337–345, (1966).

Abstract M73 from 51 J. Dairy Science 940 (No. 6), T. C. Everson et al., "Rennet Coagulation Test with a Recorded Endpoint".

(List continued on next page.)

*Primary Examiner*—Stewart J. Levy
*Assistant Examiner*—Joseph W. Roskos
*Attorney, Agent, or Firm*—Workman, Nydegger & Jensen

[57] ABSTRACT

Apparatus and methods for measuring milk coagulation time and rigidity in the manufacture of fermented dairy products such as cheese. The apparatus includes a substantially flat, disc-shaped probe which is suspended from a wire into a fermented dairy product-making vessel filled with milk. The probe is reciprocated through a small vertical distance within the coagulating milk in the vessel, and the increasing resistance to the probe communicated through the wire as the milk coagulates is continuously measured. When the measured probe resistance reaches a predetermined value, it is time to cut the curd formed by the coagulating milk. The present invention provides apparatus which can be used on both an industrial scale and a laboratory scale.

32 Claims, 4 Drawing Figures

OTHER PUBLICATIONS

Abstract 493 from Technology for A. Groman et al., "Studies on Mechanization in Cheesemaking and its Technological Effects, I. Quantitative Analysis of Physical Changes in Milk During Clotting," 21 Zesz. nauk. wyzsz. Szk. roln. Olsztyn., 347–364, (1966).

A. W. Kowalchyk et al., "Firmness of Enzymatically-Formed Milk Gels Measured by Resistance to Oscillatory Deformation", 61 J. Dairy Sci., 1375–1379 (1978).

Abstract 495 from Technology for M. Eisele et al., "The Effect of Mechanical Determination of the Cutting Time of Coagulum on Cheese Quality," 18 Zesz. nauk. wyzsz. Szk. roln. Olsztyn., 185–190, (1964).

D. G. Bynum et al., "Standardization of a Device to Measure Firmness of Curd During Clotting of Milk", 65 J. Dairy Sci., 1321–1324 (1982).

Abstract 3819 from Technology for R. J. Baker et al., "Effect of Preacidification of Skimmilk on Curd Forming Properties of Two Cultures," 50 J. Dairy Sci., 944–945, (1967).

D. J. McMahon et al., "Evaluation of Formagraph for Comparing Rennet Solutions", 65 J. Dairy Sci., 1639–1642 (1982).

Abstract 1517 from Chemistry and Physics for M. Eisele et al., "Study of the Course of Milk Coagulation by Rennet," 13 Zeszyt. nauk. Wyzsz. Szkol. roln. Olsztyn., 221–228, (1962).

J. E. Storry et al., "Development of Coagulum Firmness in Renetted Milk-A Two-Phase Process", 49 J. Dairy Res. 343–346 (1982).

Abstract 2409 from 25 Dairy Science Abstracts 338, (No. 8) for M. Eisele et al., "Study of the Process of Rennet Coagulation of Milk by a Physical Method," 13 Zeszyt. nauk. Wyzsz. Szkol. roln. Olsztyn., 237–243, (1962).

G. W. Scott Blair et al., "Physical Changes in Milk Caused by the Action of Rennet-I. Description of Apparatus for Measuring Rigidity Moduli and Internal Viscosities, Tests of Reliability and Some Observations on Synerisis", (1957).

Abstract 3300 from Chemistry and Physics for J. Budny et al., "Development of Objective Tests for Cheesemaking, II. Firmness and Visible Light Absorption Changes in Quiescent or Turbulent Coagulating Milk," 23 Zesz. nauk. wyzsz. Szk. roln. Olsztyn, 573–586, (1967).

G. W. Scott Blair et al., "Physical Changes in Milk Caused by the Action of Rennet-III. Effects of Separation, Homogenization and Pasteurization and of Varying Calcium Content on the Rigidity Moduli and Viscosities of Curd.

Abstract 3301 from Chemistry and Physics for J. Budny et al., "Development of Objective Tests for Cheesemaking, III. Measurement of Sheer Stress and Yield Value of Rennet-Coagulating Milk," 23 Zesz. nauk. wyzsz. Szk. roln. Olsztyn., 587–602, (1967).

G. W. Scott Blair et al., "A Viscometric Study of the Breakdown of Casein in Milk by Rennin and Rennet", 28 J. Dairy Res. 165–173 (1961).

J. M. de Man et al., "Measurement of the Rennet Clotting Time of Milk with an Automatic Clot-Timer," Dairy Industries 32–33, (Jan. 1964).

W. A. Southorn, "The Torsiometer-An Instrument for the Study of Gels Considered as Elastic Solids", 37 Journal of Scientific Instruments, 292–296 (1960).

J. M. de Man et al., "Effect of Certain Salts on the Stability of Skimmilk as determined by Rennet Coagulation Time and Alcohol Test," 47 Journal of Dairy Science 954–757, (1964).

J. C. Oosthuizen et al., "A Constant Speed, Fixed Angle Torsiometer for Measuring the Coagulation of Milk by Rennet", 9 S. Afr. J. Agric. Sci. 1011–1018 (1966).

J. M. de Man, "Effect of Ortho — and Polyphosphates on Milk Stability as Measured by Rennet Coagulation Time."

G. H. Richardson et al., "Rennin-Like Enzyme from Mucor Pusillus for Cheese Manufacture", 50 Journal of Dairy Science, 1066–1072 (1967).

Advertising Brochure for the "Curd-O-Meter" of Dr. R. L. Hill, (1932).

Abstract 1916 from 25 Dairy Science Abstracts 270, (No. 7) for J. Burnett et al., "A Speed-Compensated Torsiometer for Measuring the Setting of Milk by Rennet", 28 Dairy Ind., 220–223 (1963).

N. F. Olson et al., "Rheology of Milk Gels Formed by Milk-Clotting Enzymes," 42 Journal of Food Science, 669–673, (1977).

Abstract 2074 from 21 Dairy Science Abstracts 378 (No. 8) for G. W. Scott Blair, "Physical Aspects of the Clotting of Milk by Rennet", 3 Int. Dairy Congr., 1442–1447 (1959).

(List continued on next page.)

OTHER PUBLICATIONS

P. Garnot et al., "Use of Oscillatory Deformation Technique to Determine Clotting Times and Rigidities of Milk Clotted with Different Concentrations of Rennet," 47 Journal of Food Sciences, 1912–1915, (1982).

Abstract 1476 for J. Burnett et al., "Note on the Torsiometer for Measuring Setting of Milk by Rennet", 29 Dairy Ind. 97 (1964).

Se-Eok Yun et al., "Increase in Curd Tension of Milk Coagulum Prepared with Immobilized Proteases," 46 Journal of Food Science, 705–707, (1981).

Abstract 2071 from Chemistry and Physics for C. S. Landau, "Some Aspects of the Rheology of Milk Gel", 10 Brit. J. Appl. Phys., 476–481 (1959).

H. H. Sommer et al., "The Relation of Mastitis to Rennet Coagulability and Curd Strength of Milk", (1935).

Abstract 313 from 28 Dairy Science Abstracts 46 (No. 1) for R. Frentz, "The Applications of Hartet's Thrombelastograph for the Study of Milk Coagulation", 45 Lait, 489–508 (1965).

R. J. Marshall et al., "Assessment of Two Instruments for Continuous Measurement of the Curd-Firming of Renneted Milk," 49 Journal of Dairy Research, 127–135, (1982).

Abstract 395 from 27 Dairy Science Abstracts 62 (No. 2) for G. Szabo et al., "Investigation on Setting Time and Firmness of Rennet Curd", Tejipari Kutat. Kozlem, 30–45 (1962).

W. Roth et al., "A New Method for Continuous Viscosity Measurement, General Tehory of the Ultra-Viscoson," 24 Journal of Applied Physics, 940–950, (1953).

Abstracts 3399–3400 from Chemistry and Physics for J. Cesul, "Methods for Measuring the Firmness of Coagulum", 9 Przegl. mlecz., 12–16 (1961).

S. J. Rowland et al., "The Firmness of Rennet Curd: Its Measurement and Variations", (1942).

Abstract 3236 from 25 Dairy Science Abstracts 474 (No. 11) for M. Kawai et al., "Examination of the Curd Tension Test to Estimate Coagubility of Milk in the Stomach of Infant", 15 J. Jap. Soc. FD Nutr., 99–104 (1962).

J. F. Weder, "Neue Messmethode zur Bestimmung von Gelfestigkeiten", (1972).

Abstract 2211 from 25 Dairy Science Abstracts 314 (No. 8) for M. Eisele et al., "Studies of the Suitability of a Device for Objective Assessment of the Correct Time for Cutting the Coagulum", 13 Zeszyt. Nauk. Wyzsz. Szkol. Roln. Olsztyn., 229–235 (1962).

W. Schar et al., "Ein Neues Gerät zur Messung des Verfestigungsverlaufes von Milchgallerten," Technologie 15/Nr. 5, (1982).

Abstract 1902 from Chemistry and Physics for J. Jacquet et al., "Graph Recording of the Coagulation Phenomenon of Milk", 50 C.R. Acad. Agric. Fr., 1272–1280 (1964).

J. W. Doty, "The Falling Number Method — A Rapid Technigue for Malt Control", reprinted from 55 Baker's Digest No. 2, (Apr. 1981).

Abstract 1903 from Chemistry and Physics for R. V. Rao et al., "Studies on the Curd Tension of Milk", 1 J. Fd Sci. Tech., 19–22 (1964).

"Falling Number System for Determination of Alpha-Amylase Activity," an advertising brochure of Falling Number AB.

Abstract 1904 from Chemistry and Physics for T. Miyabe et al., "Curd Tension. Studies on the Curd Tension and Salt Balance in Abnormal Milk. Part II. On the Influence of Meta and Pyrophosphates", 17 J. Jap. Soc. Fd Nutr., 225–232 (1964).

W. C. Mallhot, "The Falling Number Method," Cereal Foods World, pp. 50–51, (1980).

Abstract 2018 from Chemistry and Physics for P. W. Voisey et al., "Modification of the Curd Firmness Test for Cottage Cheese," 49 J. Dairy Sci., 93–96 (1966).

K. Lorenz et al., "Effect of Altitude on Falling Number Values of Flours," 58 Cereal Chemistry, 80–82, (1981).

Abstract 190 from Bacteriology and Mycology for W. W. Overcast et al., "Tension of Curd for Selected Lactic Cultures", 48 J. Dairy Sci., 1202–1204 (1965)).

D. B. Emmons, "Manufacturing Factors That Affect Cheese Yields," presentation at Utah State Cheese Industry Conference, (1978).

Abstract 3386 from Technology for M. Eisele et al., "Effect of Mechanical Determination of the Time of Cutting the Coagulum on Cheese Quality", 18 Zesz. Nauk. Wyzsz. Szk. Roln. Olsztyn., 185–190 (1964).

C. L. Hicks et al., "Effect of Culture Media on Cheese Yield," Utah State Cheese Industry Conference, (1982).

Abstract 2672 from Chemistry and Physics for P. J. de Koning et al., "Characterization of Mixtures of Calf Rennet and Rennet Substitutes", 23 Neth. Milk Dairy J., 55–70 (1969).

APPARATUS AND METHODS FOR MEASURING MILK COAGULATION TIME AND RIGIDITY IN THE MANUFACTURE OF FERMENTED DAIRY PRODUCTS

BACKGROUND

1. The Field of the Invention

The present invention relates to apparatus and methods for measuring milk rigidity in the manufacture of fermented dairy products. More particularly, the present invention is directed to apparatus and methods for measuring the coagulation time of and the degree of milk rigidity in the manufacture of fermented dairy products such as cheese and for determining when to cut the curd formed by the coagulated milk.

Although the present invention relates to apparatus and methods for measuring milk rigidity in the manufacture of many different types of fermented dairy products, the following discussion of the present invention, as well as the discussion of the prior art, is generally in terms of cheesemaking. However, since the processes for making other fermented dairy products are closely akin to the processes for cheesemaking, it will be readily understood that the description of the present invention also pertains to the manufacture of other fermented dairy products.

2. The Prior Art

Cheese is made by the controlled coagulation and syneresis of milk. Each year, the cheesemaking industry in the United States consumes literally billions of gallons of milk for the production of cheese. Coagulation and syneresis of the milk is accomplished by an extract containing an enzyme known as rennin or chymosin, which enzyme is extracted from the fourth or true stomach of a calf. (Other suitable enzyme-containing extracts obtained from bovine, swing, and fungal sources are also used.)

Upon action by the rennin, the milk is converted into a cheese curd and whey. The activity of the rennin is enhanced or catalyzed by both heat and lactic acid. Generally, lactic acid is supplied by lactic acid-producing bacteria, such as *Streptococcus lactis* and *Streptococcus cremoris*. Such bacteria feed primarily on the lactose in milk to produce the acid needed in the manufacture of cheese.

A bulk culture of lactic acid-producing bacteria is typically prepared in a vessel known as a bulk culture tank and serves as an inoculant for the milk to be made into cheese. This bulk culture of lactic bacteria generally comprises from about 0.1% to about 5% or more of the total volume of milk to be inoculated.

Once a satisfactory lactic bacteria bulk culture has been prepared in the bulk culture tank, the bulk culture is introduced into a cheesemaking vessel containing the milk. The rennin enzyme is also added to the milk in the cheesemaking vessel, and the lactic bacteria cultures produce the necessary acid to aid the enzyme in producing cheese.

In the manufacture of fermented dairy products such as cheese, it is important to monitor the progressive coagulation of the milk in order to determine when the formed curd should be cut. One test for determining when the curd should be cut involves the insertion of a dairy thermometer into the curd at about a 45° angle. The thermometer is then lifted straight up out of the curd; if a clean split of the curd results, the curd strength or tension has developed to the desired point for cutting the curd. This curd is typically cut by pulling cutting wires or bars through the curd.

The timing involved in the cutting of the curd is important in terms of obtaining the maximum cheese yield. For example, if the curd is cut too soon, many of the cheese-forming solids may be lost in the whey, resulting in less product. If the curd is cut too late, it may be difficult to pull the cutting wires or bars through the curd to form uniform curd particles. Moreover, if the curd is cut too late, the resulting curd particles are so firm that it takes a relatively long period of time for the whey to be released from the curd particles. The result is that a substantially longer period of time is required to obtain a curd product of the desired moisture content.

A variety of factors are involved in determining the exact coagulation rate of the milk; e.g., the composition of the milk used to make the cheese, the activity of the lactic bacteria bulk culture, the particular enzyme used to coagulate the milk, the temperature within the cheesemaking vessel, the salt concentration of the milk and lactic bacteria bulk culture, and the previous enzymatic activity in the milk. These numerous variables make it difficult to accurately predict the coagulation rate, and thus the proper time at which the curd should be cut.

After the curd has been cut, the cut curd is generally allowed to settle and heal until the freshly cut curd surfaces harden slightly. Thereafter, the cut curd is then agitated to facilitate whey removal and prevent curd particle fusion until the desired cheese moisture is obtained. By allowing the curd surfaces to harden during healing of the curd, shattering of the curd particles is reduced when the cut curd is agitated.

As discussed below, many different apparatus have been developed for measuring milk coagulation time to help predict the proper time for cutting the curd in the manufacture of fermented dairy products such as cheese. However, these prior art devices have not been commercially accepted, and most cheese producers cut the curd after a set period of time, whether or not it is the ideal time for cutting the curd. The result is often wasteful. While there are some devices for determining the time to cut the curd, there has not, unfortunately, been any adequate instrumentation which can determine when proper healing of the curd has occurred so that agitation can begin. Again, most cheesemakers use an "educated guess" at this time.

In one device developed to measure milk coagulation time, the degree of coagulation is estimated by measuring the drip rate of the coagulating milk through a capillary tube at various time intervals. (See, e.g., G. Scott Blair et al., "A Simple Method for Detecting an Early Stage in Coagulation of Rennetted Milk," 30 J. Dairy Res. 383–390 (1963).) In another apparatus, sound waves are passed through the milk as it coagulates and the increase in the velocity of the sound waves is measured as an indication of the extent of coagulation. (See, e.g., abstract M73 from 51 J. Dairy Sci. 940 (No. 6), T. Everson et al., "Rennet Coagulation Test with a Recorded Endpoint.")

Milk coagulation monitoring apparatus have also been developed wherein the drag on an object pulled through the coagulating milk is measured or wherein the resistance to an oscillating wire within the coagulating milk is measured to indicate the extent of coagulation. (See, e.g., D. McMahon et al., "Evaluation of Formagraph for Comparing Rennet Solutions," 65 J. Dairy Sci. 1639–1642 (1982).)

Certain apparatus employing diaphragms have been developed which measure the resistance of the coagulating milk to oscillatory deformation. (See, e.g., A. Kowalchyk et al., "Firmness of Enzymatically-Formed Milk Gels Measured by Resistance to Oscillatory Deformation," 61 J. Dairy Sci. 1375–1379 (1978).) In one such apparatus, two juxtaposed diaphragms are placed into the coagulating milk sample; one diaphragm (the transmitting diaphragm) oscillates and sends pulses through the coagulating milk to the other diaphragm (the receiving diaphragm). The extent of the pulses or deformations transmitted by the transmitting diaphragm through the coagulating milk to the receiving diaphragm is indicative of the firmness of the milk coagulum.

Other apparatus, typically referred to as torsiometers, involve the use of a cylinder which is suspended into the coagulating milk and oscillated through a fixed angle. (See, e.g., J. Oosthuizen et al., "A Constant Speed, Fixed Angle Torsiometer for Measuring the Coagulation of Milk by Rennet," 9 S. Afr. J. Agric. Sci. 1011–1018 (1966).) The restraining drag on the rotating cylinder is measured as the milk coagulates. The increasingly larger torque force needed for oscillating the cylinder through the fixed angle is indicative of the degree of coagulation.

A thrombelastrograph is yet another device which has been used for measuring the coagulation time of milk. (See, e.g., N. Olson et al., "Rheology of Milk Gels Formed by Milk-Clotting Enzymes," 42 Journal of Food Science 669–673 (1977).) In a typical thrombelastrograph device, two coaxial cylinders are placed within the sample of coagulating milk. The outer cylinder is caused to rotate; thus, as coagulation occurs, the rotational motion of the outer cylinder is transferred to the inner cylinder which is suspended by a wire. A mirror on the wire supporting the inner cylinder in the milk coagulum reflects a light beam to photosensitive recording paper, thereby recording the oscillations of the inner cylinder which are indicative of the degree of coagulation.

Still another apparatus used in the prior art is the vibrating-reed viscometer. (See, e.g., R. Marshall et al., "Assessment of Two Instruments for Continuous Measurement of the Curd-Firming of Renneted Milk," 49 J. Dairy Res. 127–135 (1982).) The vibrating-reed viscometer apparatus measures the voltage which is required to keep a reed vibrating within the milk sample as it coagulates.

Despite the numerous apparatus and methods which have been developed in the prior art for measuring the progressive coagulation of milk in making fermented dairy products such as cheese, several significant problems are still encountered in the prior art apparatus and method. One important limitation of the prior art is that, typically, the prior art apparatus are designed for testing milk samples on a laboratory scale and not on an actual industrial operating scale.

Such laboratory scale apparatus often do not adequately predict the actual coagulation times which will be encountered in industrial operations. For example, the conditions within an industrial scale cheesemaking vat are considerably different from those conditions within the laboratory-sized receptacles which are often used to test the coagulation time of milk in the prior art. Thus, the laboratory measurements provided by such prior art apparatus have often not provided accurate data from which to predict the coagulation time and curd cutting time in making cheese and other fermented dairy products on an industrial scale.

A typical cheesemaking vat holds from about 2300 to about 6400 gallons of milk (representing approximately 20,000–55,000 pounds of milk), and thus, significant movements of these large volumes of milk within the vat are typically experienced during cheesemaking. The prior art apparatus have encountered significant difficulty in making accurate and reproducible measurements within the cheesemaking vat, because the motion of the milk within the vat disturbs the operation of the apparatus. This is one important reason why the prior art has dealt primarily with laboratory scale apparatus.

In addition, any device which is used in the large commercial cheesemaking vats cannot be overly complicated and fragile. Unfortunately, most of the prior art devices are complicated, fragile, and overly sensitive to typical setup procedures and operating conditions.

As a result, the prior art apparatus are typically either limited to laboratory scale application (which experimental results are often difficult to extrapolate to the industrial scale) or do not provide accurate measurements of the milk coagulation when placed directly into large industrial scale, fermented diary product-making vessels, e.g., into a cheesemaking vat. The prior art has generally thus not provided accurate and reproducible coagulation time data for cheese produced on an industrial scale and for other fermented dairy product-making operations.

Another problem encountered in the prior art is that of obtaining a quiescent state for the milk by the time that coagulation begins. Typically, when the lactic bacteria bulk culture and enzyme are added to the milk, the milk is thoroughly agitated so as to mix the bulk culture and enzyme into the milk. As a result, significant movements are experienced within the milk in the cheesemaking vat. Such movement is undesirable during coagulation of the milk since motion disturbs the forming curd and a loss of solids in the formed curd may result from such disturbance. Hence, it is desirable to have minimal motion in the milk during the coagulation of the milk. Baffles or other restriction devices are often installed into the cheesemaking vat in order to obtain quiescence of the milk before significant coagulation has begun. However, the prior art has not provided any method for determining the time elapsed before the milk is rendered quiescent so that it may be determined if such baffles or other restriction devices are needed.

From the foregoing, it will be appreciated that what is needed in the art are apparatus and methods for measuring milk coagulation times and curd firming rates in the manufacture of fermented dairy products (such as cheese), wherein the apparatus and method can be conveniently and simply utilized directly in large scale industrial operations, as well as in laboratory scale experiments.

Additionally, it would be a significant advancement in the art to provide such apparatus and methods which are not significantly affected by the movement of the coagulating milk within the industrial scale, fermented dairy product-making vessel, and which provide accurate and reproducible coagulation time data on both the industrial scale and the laboratory scale.

It would be a further advancement in the art to provide an apparatus and method for determining when adequate healing of the cut curd has occurred and when the cut curd should be agitated. Such apparatus and methods are disclosed and claimed herein.

It would be yet another advancement in the art to provide an apparatus and method for determining when the agitated milk, lactic bacteria bulk culture, and enzyme have become quiescent within a cheesemaking vat so as to determine whether or not mechanical restriction devices are needed to accelerate quiescence.

BRIEF SUMMARY AND OBJECTS OF THE INVENTION

The present invention relates to apparatus and methods for measuring milk rigidity in the manufacture of fermented dairy products such as cheese. In the presently preferred embodiment of the apparatus of the present invention, a horizontally-oriented, flat, disc-shaped probe is suspended by a wire into a vessel of coagulating milk, such that the flat horizontal surfaces of the probe are substantially parallel to the upper surface of milk in the vessel.

A mechanical driving force is applied to the wire so as to cause the wire, and thus the probe attached thereto, to reciprocate up and down in a vertical direction. A strain gage in communication with the wire measures the amount of resistance on the wire, and thus the amount of resistance experienced by the probe as it reciprocates in the vessel of coagulating milk.

The measured resistance is communicated from the strain gage to a recording device for continuously monitoring the increasing resistance to the movement of the probe, which is directly related to the degree of milk coagulation. The apparatus is calibrated such that when the probe resistance reaches a predetermined value, a warning light may be lit or an alarm may be sounded to signal that it is time to cut the curd.

After the curd has been cut, it is allowed to settle and heal. During this time, the probe can be reinserted into the cut curd and reciprocated as the curd settles. During settling of the curd, the baseline of the measured probe resistance begins to drift; when this drift reaches a predetermined value, an alarm can be programmed to sound again, thereby signaling that it is time for agitation of the settled curd. The present invention may also be used to determine the final gel rigidity of the formed curd.

In the presently preferred embodiment of the apparatus, the surface of the probe is constructed of a material which substantially adheres to the coagulating milk so as to provide for more accurate measurements of the degree of coagulation by preserving the structural integrity of the coagulating milk and forming curd immediately around the probe. Additionally, the horizontally flat configuration of the probe and the vertical reciprocal motion of the probe serve to provide an apparatus which is not substantially affected by the movement of the milk within the vessel.

It is, therefore, an object of the present invention to provide apparatus and methods for accurately measuring milk coagulation times and curd firming rates in the manufacture of fermented dairy products such as cheese wherein the apparatus and methods can be conveniently and easily applied to industrial scale operations, as well as to laboratory scale experiments.

Another object of the present invention invention is to provide apparatus and methods for measuring milk coagulation times and curd firming rates in the manufacture of fermented dairy products such as cheese, which apparatus and methods are not significantly affected by the movement of the coagulating milk within the fermented dairy product-making vessel.

A further object of the present invention is to provide apparatus and methods for providing accurate and reproducible coagulation time data in the manufacture of fermented dairy products such as cheese.

Still another object of the present invention is to provide an apparatus and method for determining when the curd should be cut in the manufacture of fermented dairy products such as cheese, and for determining when adequate healing of the curd has occurred such that the cut curd should be agitated.

Yet another object of the present invention is to provide an apparatus and method for measuring milk rigidity in the manufacture of fermented dairy products such as cheese wherein the coagulating milk and forming curd are not cut, deformed, or otherwise disturbed by the apparatus in a manner which would substantially affect the structural integrity of the coagulating milk and forming curd and thereby affect the accuracy of the milk coagulation measurements.

Another object of the present invention is to provide an apparatus and method for measuring the time necessary in order for the agitated milk, lactic bacteria bulk culture, and enzyme within a cheesemaking vessel to reach a quiescent state, thereby giving an indication as to whether or not restriction devices are needed to prevent significant movements within the milk during coagulation.

These and other objects and features of the present invention will become more fully apparent from the following description and appended claims, taken in conjunction with the accompanying drawings.

DETAILED DESCRIPTION OF THE PREFERRED EMBODIMENTS

Reference is now made to the drawings wherein like parts are designated with like numerals throughout.

Figure 1:
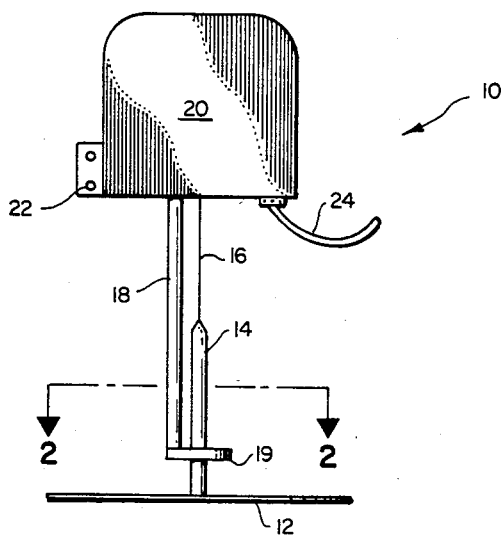
FIG. 1 is a side elevational view of one presently preferred embodiment of the present invention used to measure milk rigidity in the industrial scale manufacture of fermented dairy products such as cheese.
Figure 2:
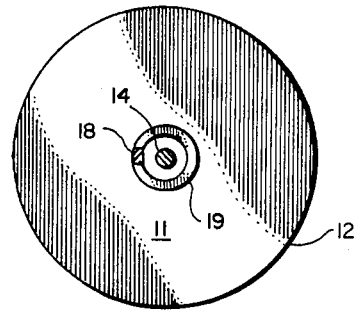
FIG. 2 is a cross-sectional view of the embodiment of FIG. 1 taken along line 2—2.

Referring now to FIGS. 1 and 2, one presently preferred embodiment of the apparatus and method of the present invention, generally designated 10, is illustrated. Apparatus 10 is designed for the industrial scale application of the present invention for measuring milk rigidity in the manufacture of fermented dairy products such as cheese. The apparatus includes a substantially flat, disc-shaped probe member 12 which is connected to a wire 16 by a connecting rod 14. Wire 16 is connected to a drive and sensing unit 20.

Housed within driving and sensing unit 20 are conventional driving means (not shown) for imparting a vertically reciprocating motion to wire 16. Such a reciprocating motion may, for example, be applied to wire 16 by a motor (not shown) through a cantilever arm (not shown). By way of example only, one motor which has been found to be suitable for purposes of the driving means of the present invention is the ac timing motor made by Synchron or the ac timing motor made by Haydon, both sold by American Design Corporation, New York N.Y. Typically, the timing motor is then coupled to a set of gears (not shown) which are in turn coupled to a reciprocal drive rod (not shown). It will be recognized, however, that the foregoing is given by way of example only, and that many other suitable driving means for imparting a reciprocating motion to wire 16 are commercially available and may be used in accordance with the present invention.

Driving and sensing unit 20 also includes means (not shown) for sensing the resistance placed on probe 12 as communicated through rod 14 and wire 16. In particular, a strain gage has been found to be suitable for purposes of the sensing means of the present invention and is placed in communication with wire 16 within driving and sensing unit 20 as well as in communication with the reciprocal drive rod when used with the exemplary timing motor, gears, and reciprocal drive rod discussed above. For example, the strain gage may be wired as a half-bridge and applied to the cantilever arm discussed in the example above.

One strain gage which has been found to work well for purposes of the present is strain gage type EA-06-250BG-120, sold by Micro-Measurements Division of the Measurements Group of Raleigh, North Carolina. Of course, it will again be appreciated that this particular strain gage and the foregoing examples are given by way of example only, and that many other strain gages are commercially available and may be used in accordance with the present invention.

It will also be appreciated that there are many other sensing means which are well-known and commercially available for measuring the resistance to wire 16, and that any other suitable means for so measuring the resistance may be employed in accordance with the present invention. For example, a linear variable differential transformer (LVDT) could be used in lieu of a strain gage.

A suitable power-driven reel (not shown) may also be housed within driving and sensing unit 20 to adjust the effective length of wire 16. The reel is activated to lower the probe into the milk so as to initiate measurement of the milk rigidity, and it also acts to withdraw the probe from the curd prior to curd cutting. If desired, wire 16, rod 14, and probe 12 can be charged with a low power electrical charge to detect when probe 12 contacts the milk. Microprocessor controls (not shown) can then position probe 12 to the proper depth in the milk by driving the reel the desired additional distance before stopping. This allows for proper positioning of the probe 12 irrespective of the relative fill of the cheesemaking vat.

Optionally, apparatus 10 may further include a proberestraining member 18 mounted to driving and sensing unit 20. Restriction member 18 includes a restraining ring 19 through which rod 14 and/or wire 16 extends. The function of restraining member 18 and restraining ring 19 are to prevent substantial movement of wire 16 and rod 14, and thus of probe 12, in the horizontal direction while the probe is being cleaned or is not in use.

Apparatus 10 also includes a bracket 22 for attachment of the apparatus to the cheesemaking vessel (not shown) and a cable 24 for providing power to the driving and sensing unit 20, for receiving electrical resistance data from the strain gage, and for communicating the resistance data to a digital or analog recorder (not shown) or digital analog alarm (not shown). Bracket 22 has been found useful in the attachment of apparatus 10 to an open cheesemaking vat; however, apparatus 10 may be mounted to a cheesemaking vat in other fashions as well. For example, attachment of the apparatus of the present invention to a closed cheesemaking vat may be accomplished by mounting the apparatus to the opening in the top of the closed cheesemaking vat using flanges as shown in FIG. 4.

Figure 4:
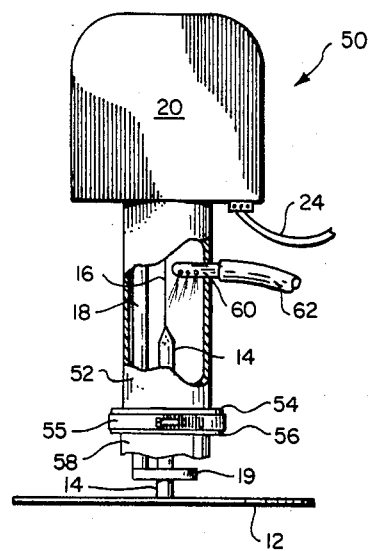
FIG. 4 is a side, partial break-away view of a second preferred embodiment of the present invention used to measure milk rigidity in the industrial scale manufacture of fermented dairy products such as cheese.

As seen in FIG. 4, a second preferred embodiment of the apparatus of the present invention which is adapted for mounting to a closed cheesemaking vat, is generally designated 50. Apparatus 50 is substantially similar to apparatus 10 of FIG. 1, except that apparatus 50 is mounted to the opening of a closed vat 58 by a pair of flanges 54 and 56 which are secured together by a screw clamp 55. Additionally, apparatus 50 includes a vertical pipe 52 which surrounds rod 14, wire 16, restraining member 18 and restraining ring 19. Mounted within pipe 52 is a perforated spray nozzle 60 connected to a conduit 62 through which cleaning solution is supplied. After operation of the apparatus, the wire 16, rod 14, and probe 12 may be cleaned by introducing cleaning solution from conduit 62, through spray nozzle 60, and into vertical tube 52. The cleaning solution is thus sprayed downwardly through tube 52 so as to thoroughly rinse wire 16, rod 14, and probe 12. Acid, alkali, chlorine, or any other suitable rinse solution may be used as the cleaning solution.

One of the key features of the present invention is the configuration and construction of probe 12, as it is used to provide a vertically moving planar surface through the coagulating milk. As seen in both FIGS. 1 and 2, probe 12 is preferably disc-shaped in configuration, having a substantially flat, horizontal upper surface 11 and a substantially flat, horizontal lower surface (not shown). Thus, probe 12 is preferably configured so as to have a substantially large surface area to volume ratio such that substantial contact between the probe and the coagulating milk is maintained during operation of the probe. The relatively large planar surface area of the probe provides for more sensitive readings by the sensing unit 20.

In one presently preferred embodiment, probe 12 is constructed of stainless steel, for example, number four finish stainless steel. However, it will be appreciated that any suitable rigid material may be used in the construction of probe 12. Stainless steel such as number four finish stainless steel is presently preferred since the coagulating milk and forming curd within the cheesemaking vat adhere to probes made of this type of material. Such adherence is desirable for reasons explained in more detail herein. It will be recognized that stainless steel is given by way of example only, and that there may be other materials suitable for forming probe 12 which will provide a surface that adheres to the coagulating milk and forming curd in accordance with the present invention.

In one presently preferred embodiment of the present invention, probe 12 is configured as a flat disc of about four to about six inches in diameter with a weight of about 150 to about 300 grams, and is connected to a rod having a diameter of about 0.75 inches to about 1.25 inches and a length of about 5 to about 9 inches. It will be appreciated that these dimensions are given by way of example only and should not be considered limiting in any way. For example, a probe having a larger diameter could be used to obtain greater sensitivity in measurement. It has been found that for typical cheesemaking vats of 6400 gallons of milk (representing about 55,000 pounds of milk), a probe having a diameter of about 6 inches provides sufficient sensitivity when utilized according to the method of the present invention.

It will be appreciated that the exact size of the probe will depend upon the particular application involved. Probes with a larger diameter provide more sensitivity. It has been found that a larger probe diameter is often preferable for making buttermilk, yogurt, and sour cream where the initial viscosity of the milk is not as great as for other fermented dairy products, thus requiring more probe sensitivity. Probes with a smaller diameter may be more desirable for laboratory scale applications or for highly viscous milk products such as ultrafiltered milk retentate.

The operation of the apparatus of the present invention and one presently preferred embodiment of the method of the present invention will be best understood from the following discussion. Apparatus 10 is first mounted to the cheesemaking vessel or vat by bracket 22 or any other suitable means. The milk, cheesemaking enzyme, and lactic bacteria culture are introduced into the cheesemaking vat and thoroughly agitated.

After agitation, there is significant movement of the milk within the cheesemaking vat. This movement affects the probe measurement slightly; when the measured probe resistance signal finally stabilizes, this signals that the milk has a reached quiescent state. By measuring the time required for the milk to become quiescent, it can be determined if baffles or other restriction devices are needed within the cheesemaking vat such that significant movements of the milk will not be experienced during coagulation of the milk.

Once agitation is complete, the milk is allowed to settle and probe 12 is lowered into the cheesemaking vat by mechanically lowering wire 16, rod 14, and probe 12 to the desired immersion depth. Probe 12 is lowered to a depth such that the probe is about 3 to about 9 inches below the surface of the milk in the cheesemaking vat; the horizontal upper surface 11 of the probe is preferably parallel to the surface of the milk in the cheesemaking vat in order to minimize disturbance to and horizontal movement of the probe during operation. In one presently preferred application, the probe is immersed to a depth of about six inches below the surface of the milk.

Once lowered into the milk to the desired level, a vertical reciprocating motion is imparted to probe 12 by activating the driving means within drive and sensing unit 20. The up and down vertical motion of probe 12 is preferably accomplished through a distance of about 1 to about 30 millimeters at a rate of about 3 to about 10 cycles per minute. It will be appreciated that other distances and cycles for the movement of the probe may be possible, and that these parameters are given by way of example only. In choosing the distance traveled by the probe and the rate at which the probe reciprocates, consideration should be given to minimizing disturbance to the milk coagulum and to developing a probe resistance substantial enough for detection and measurement.

As the milk begins to coagulate within the cheesemaking vat, resistance to the vertical movement of the reciprocating probe 12 begins to develop. This resistance is continuously measured by the strain gage in drive and sensing unit 20, and the measurement of resistance is communicated by cable 24 to the printout recorder. As the milk coagulates, the amount of resistance to the probe movement will increase.

After repeated cheesemaking operations, apparatus 10 may be calibrated to the precise value of the measured probe resistance where coagulation has reached the point where the curd should be cut. If desired, an alarm system may be connected to the printout recorder so as to light up a warning light or sound an alarm when the measured resistance reaches this determined calibration value, signaling that the curd is ready for cutting. Alternatively, automatic curd cutting equipment could be activated when this value is reached.

The apparatus and method of the present invention provide not only for the accurate measurement of the degree of coagulation of the milk, but also provide surprisingly reproducible results. Thus, precise calibration of the apparatus is possible, thereby resulting in accurate and reproducible curd cutting times in different cheesemaking runs. Such accuracy and reproducibility have not heretofore been possible in industrial scale cheesemaking operations.

Of course, it will be appreciated that the calibration point may be significantly different for the different fermented dairy products which are made using the present invention. Moreover, the precise calibration point will also depend upon the composition of the milk used, the nature and concentration of the lactic bacteria employed, and other factors. One of the important advantages of the present invention is that, regardless of the type of fermented dairy product being made and the various operating conditions used, the apparatus and methods of the present invention provide for precise calibration in any given application to determine when the curd should be cut. Thus, the present invention provides methods for determining the precise curd cutting time for each individual application in the manufacture of fermented dairy products, providing great improvements over the prior art system of simply cutting the curd after a certain period of time has elapsed.

The novel configuration and operation of the probe of the present invention are important reasons for the accuracy and reproducibility achieved by the present invention. Since the coagulating milk and forming curd adhere to the surface of the probe, the curd is only temporarily deformed through a small distance by the reciprocating motion of the probe. Because of the novel probe configuration of the present invention, the curd is not significantly cut by the reciprocating motion of the probe, and the structural integrity of the curd is not otherwise significantly destroyed. The result is that the structural integrity of the coagulating milk and forming curd immediately around the probe is preserved so that error in measuring the rate of coagulation in this area is minimized.

Moreover, because measurement of the resistance of the probe is done in a vertical direction, horizontal movements of the milk within the cheesemaking vat do not substantially disturb the operation of the apparatus. Additionally, the fact that the coagulating milk and forming curd adhere to the probe further serve to minimize the effects of the moving milk within the cheesemaking vat.

Before cutting the curd, it is usually best to remove probe 12 from the formed curd by raising wire 16 and probe 12. After the curd has been cut, the curd is allowed to settle and heal. During healing, a thin film forms at the surfaces of the cut curd particles and the surfaces begin to harden. Sufficient hardening must occur before the cut curd is agitated or the curd particles will tend to shatter upon agitation. During this settling time, probe 12 is again lowered into its original position within the curd in the cheesemaking vat and is caused to reciprocate. The resistance to the reciprocating probe is then measured as the curd settles and heals.

During settling and healing of the curd, the curd begins to shrink downwardly. The result is that the reciprocating probe experiences increasing pressure or resistance by the shrinking curd as it travels in the upward direction and decreasing resistance as it travels in the downward direction. Thus, the baseline of the measured resistance to the probe as recorded by the printout recorder begins to drift. The amount of this drift is indicative of the amount of settling and healing of the curd which has occurred. Thus, when the baseline of the measured probe resistance has drifted to a predetermined value, a light may be lit or an alarm may again be sounded, if desired, to signal that it is time for the cut curd to be agitated. Alternatively, agitation may be automatically started at the predetermined value.

The apparatus of the present invention may also be used to determine the final theoretical gel rigidity of the cheese curd product. The final gel rigidity, represented as $G_{max}$, has been defined according to the following equation:

$$G = G_{max} e^{-lambda/t} \quad (1)$$

In equation (1) above, G represents the pseudo modulus of gel rigidity as generated by the apparatus of the present invention, e represents the base of the system of natural logarithms, lambda is the time required after coagulation for the modulus to equal $G_{max}$, and t is the time which has elapsed after the coagulation and curd cutting point.

Another equation has been offered for calculating the final gel rigidity. This equation is as follows:

$$G = G_{max} e^{-Tau/k(t-Tau)} \quad (2)$$

In equation (2) above, G represents the pseudo modulus of gel rigidity as generated by the apparatus of the present invention, e is the base of the system of natural logarithms, Tau is the calculated coagulation and curd cutting time, k is the relative rate of initial curd firming, and t is the time subsequent to enzyme addition.

$G_{max}$ or the final gel rigidity of the cheese curd product is indicative of the amount of "effective casein" in the cheese product. Effective casein may be defined as the total amount of casein in the final cheese curd product. During the cheesemaking process, a portion of the casein may be broken down, or "solubilized+ so that the protein escapes in the whey, thus rendering less total cheese curd product. Solubilized or denatured casein forms, for example, due to the action of the proteolytic activity of the lactic bacteria, the action of the proteolytic enzymes, the use of citrate and phosphate salts in some lactic bacteria culture media, and other factors. Since solubilized casein is often lost to the whey and does not end up in the cheese curd product, it is desirable in cheesemaking operations to minimize the amount of solubilized casein formed, which is reflected in the value of $G_{max}$. Thus, it is desirable in cheesemaking operations to carefully monitor the value of $G_{max}$ so as to calculate the effective protein content of the milk.

The present invention provides such a method for calculating $G_{max}$. To do this, one need only measure the time and G values prior to curd cutting using the present invention and then use these values for the G and t variables of equations (1) and (2) above.

Figure 3:
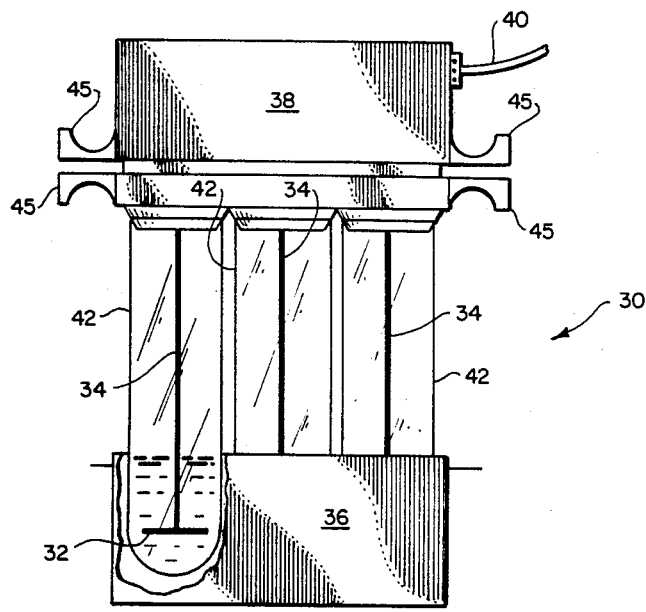
FIG. 3 is a side elevational view of one presently preferred embodiment of the present invention used to measure milk rigidity in samples of coagulating milk on a laboratory scale.

A laboratory scale model of the present invention which can be used to perform substantially the same function as the industrial scale model, is illustrated in FIG. 3 and is generally designated 30. Milk is placed into a series of test tubes 42, the bottom ends of which are lowered into an aluminum heating block 36. Each test tube 42 has a small disc-shaped probe 32 suspended into the milk within the tube, each probe 32 being supported by a rod 34.

A nonwettable material may be placed around the upper periphery of probe 32. This allows for pipetting rennet or other coagulant or chemical atop probe 32 and for the simultaneous inoculation of these substances into each of tubes 42. The rods 34 are fixed in place by manually closing a pair of clamps 45, thus allowing inoculation, mixing, and initiation of test timing.

Driving and sensing means 38 are provided for imparting a reciprocal motion to each rod 34 and probe 32, and for sensing the resistance to each probe 32 through each rod 34, in substantially similar fashion to the embodiment of FIG. 1. A cable 40 provides electrical power for the driving means and provides for communication of the measured probe resistance data from the sensing means to a printout recorder (not shown).

The operation of apparatus 30 is substantially similar to the operation of apparatus 10. The driving means are activated so at to impart a vertical reciprocating motion to probes 32, a coagulant is pipetted into each milk sample and the milk coagulation rate within each test tube 42 is calculated by measuring the resistance to each probe 32 in sensing unit 38.

The laboratory scale model of the present invention has particular utility in calculating the $G_{max}$ value for various milk samples, and in determining the ideal amounts of coagulant and other chemicals (e.g., calcium chloride) to add in the cheesemaking process. By using the laboratory application of the present invention to measure the rate of milk coagulation in various milk samples, the final gel rigidity or $G_{max}$ value can be calculated, giving an indication as to the final protein value of cheese which could be made from the milk. Thus, such a laboratory analysis can provide a method for determining which samples of milk will be best suited for the purposes of cheesemaking and what adjustments might be made to improve the cheesemaking operation.

From the foregoing, it will be appreciated that the present invention provides apparatus and methods for accurately and reproducibly measuring milk coagulation times and curd firming rates in the manufacture of virtually any fermented dairy product (such as cheese) and that advantageously, these apparatus and methods can be conveniently and simply utilized directly in large scale industrial operations, as well as in laboratory scale experiments. Additionally, it will be appreciated that the present invention further provides apparatus and methods, not previously available, wherein the proper healing time of the cut curd can be monitored so as to determine when the cut curd should be agitated.

The present invention may be used to measure milk coagulation times and milk rigidity in the manufacture of virtually any fermented dairy product. For example, the apparatus of the present invention has been used successfully to measure coagulation parameters in milk for Cheddar cheese, Swiss cheese and directly acidified cottage cheese. It can also be used to measure, for example, coagulation properties in ultrafiltered milk, buttermilk, yogurt, sour cream, and other fermented dairy products.

The present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed and desired to be secured by United States Letters Patent is:

1. An apparatus for measuring rheological parameters of coagulating milk, comprising:
   a probe which is substantially flat in a horizontal direction;
   means for suspending said probe into a vessel of coagulating milk;
   means for reciprocating said probe in a vertical direction; and
   means for measuring the resistance to the probe as it reciprocates through the coagulating milk.

2. An apparatus as defined in claim 1 wherein said probe is disc-shaped.

3. An apparatus as defined in claim 1 wherein at least the exterior surface of said probe is constructed of a material which substantially adheres to the coagulating milk.

4. An apparatus as defined in claim 3 wherein said probe is made of stainless steel.

5. An apparatus as defined in claim 3 wherein said probe is made of number four finish stainless steel.

6. An apparatus as defined in claim 1 wherein said measuring means is a double strain gage.

7. An apparatus as defined in claim 1 wherein said measuring means is a linear variable differential transformer.

8. An apparatus as defined in claim 1 wherein said vessel is a test tube containing a relatively small volume of milk.

9. An apparatus for measuring milk rigidity in a vessel of coagulating milk during the manufacture of fermented dairy products, comprising:
   a disc-shaped probe which is substantially flat in a horizontal direction;
   a wire attached to said probe, said wire serving to suspend said probe into the vessel of coagulating milk such that the probe is substantially parallel to the upper surface of the milk in the vessel;
   means for reciprocating said wire in a vertical direction so at to impart a vertically reciprocating motion to the probe within said vessel; and
   means in communication with said wire for measuring the resistance to said probe as it reciprocates through the coagulating milk, the coagulating milk adhering to the exterior surface of the probe such that the coagulating milk moves with the probe as it reciprocates, the measured resistance thus providing a measurement of the rigidity of the coagulating milk.

10. An appartus as defined in claim 9 wherein at least the exterior surface of said probe is constructed of a material which substantially adheres to the coagulating milk.

11. An apparatus as defined in claim 10 wherein said probe is constructed of number four finish stainless steel.

12. An apparatus as defined in claim 9 wherein said probe has a substantially large surface area to volume ratio.

13. An apparatus as defined in claim 9 further comprising means for printing out the measured probe resistance.

14. An apparatus as defined in claim 9 further comprising an alarm which is sounded when the measured probe resistance reaches a predetermined level.

15. An apparatus for measuring milk rigidity in a vessel of coagulating milk during the manufacture of cheese, comprising:
   a disc-shaped probe which is substantially flat in a horizontal direction;
   a wire attached to said probe, said wire serving to suspend said probe into the vessel of coagulating milk such that the probe is substantially parallel to the upper surface of the milk in the vessel;
   means for reciprocating said wire in a vertical direction so as to impart a vertically reciprocating motion to the probe within said vessel; and
   means in communication with said wire for measuring the resistance to said probe as it reciprocates through the coagulating milk, the coagulating milk adhering to the exterior surface of the probe such that the coagulating milk moves with the probe as it reciprocates, the measured resistance thus providing a measurement of the rigidity of the coagulating milk.

16. A method for measuring rheological parameters of coagulating milk, comprising the steps of:
   suspending a probe which is substantially flat in a horizontal direction into a vessel of coagulating milk;
   reciprocating the probe in a vertical direction within the vessel; and
   measuring the resistance to the probe as it reciprocates through the coagulating milk.

17. A method as defined in claim 16 wherein the probe has a substantially large surface area to volume ratio so as to provide substantial contact between the probe and the coagulating milk.

18. A method as defined in claim 16 wherein at least the exterior surface of said probe is constructed of a material which substantially adheres to the coagulating milk such that the structural integrity of the coagulating milk is substantially preserved as the probe reciprocates.

19. A method as defined in claim 18 wherein said probe is constructed of stainless steel.

20. A method as defined in claim 18 wherein said probe is constructed of number four finish stainless steel.

21. A method as defined in claim 16 wherein the resistance to the probe is measured by a strain gage.

22. A method as defined in claim 16 wherein the resistance to the probe is measured by a linear variable differential transformer.

23. A method as defined in claim 16 wherein the configuration and operation of the probe provide for accurate measurement of the resistance to the probe as it reciprocates in a vertical direction, even when there is substantial movement of the coagulating milk within the vessel.

24. A method as defined in claim 16 wherein the measured resistance to the probe is used to determine when a curd formed by the coagulating milk is to be cut.

25. A method for measuring the rigidity of coagulating milk, comprising the steps of:
   suspending a substantially flat probe into a vessel of coagulating milk;
   reciprocating the probe in a vertical direction within the vessel;
   measuring the resistance to the probe as it reciprocates through the coagulating milk, the measured resistance to the probe being used to determine when a curd formed by the coagulating milk is to be cut;
   cutting the curd;
   allowing the cut curd to settle;
   determining when the cut curd should be agitated by observing the drift of the baseline of the measured resistance to the probe during settling of the cut curd.

26. A method as defined in claim 24 wherein the determined curd cutting time is used to determine the final gel rigidity of the curd.

27. A method as defined in claim 16 further comprising the step of observing when the initially measured probe resistance has stabilized so as to determine when the milk has reached a quiescent state within the vessel.

28. A method for measuring milk rigidity in a vessel of coagulating milk during the manufacture of cheese, comprising:
   suspending a disc-shaped probe which is substantially flat in a horizontal direction into the vessel of coagulating milk;
   reciprocating the probe in a vertical direction within the vessel; and
   measuring the resistance to the probe as it reciprocates through the coagulating milk, the coagulating milk adhering to the exterior surface of the probe such that the coagulating milk moves with the probe as it reciprocates, the measured resistance thus providing a measurement of the rigidity of the coagulating milk.

29. A method for manufacturing fermented dairy products, comprising the steps of:
   introducing a lactic bacteria culture and a fermented dairy product-making enzyme into a vessel containing milk, the enzyme acting to coagulate the milk within the vessel;
   suspending a disc-shaped probe which is substantially flat in a horizontal direction into the coagulating milk within the vessel;
   reciprocating the probe in a vertical direction within the vessel;
   measuring the resistance to the probe as it reciprocates through the coagulating milk; and
   cutting a curd formed by the coagulating milk when the measured resistance reaches a predetermined value.

30. A method as defined in claim 29 further comprising the steps of:
   allowing the cut curd to settle;
   allowing the probe to reciprocate through the cut curd;
   observing the drift of the baseline of the measured resistance to the reciprocating probe as the curd settles; and
   agitating the cut curd when the baseline drift reaches a predetermined value.

31. An apparatus for measuring rheological parameters of coagulating milk, comprising:
   a probe having a substantially flat, planar surface;
   means for suspending said probe into a vessel of coagulating milk;
   means for reciprocating said probe; and
   means for measuring the resistance to the probe as it reciprocates through the coagulating milk, the coagulating milk adhering to the exterior surface of the planar probe such that the coagulating milk moves with the probe as it reciprocates, the measured resistance thus providing a measurement of rheological parameters of the coagulating milk.

32. An apparatus as defined in claim 1 further comprising means for determining when a curd formed by the coagulating milk is to be cut.

* * * * *

UNITED STATES PATENT AND TRADEMARK OFFICE
CERTIFICATE OF CORRECTION

PATENT NO. : 4,542,645

DATED : September 24, 1985

INVENTOR(S) : Gary H. Richardson et al.

It is certified that error appears in the above-identified patent and that said Letters Patent is hereby corrected as shown below:

Column 1, line 37, "swing," should be --swine,--
Column 3, line 57, "method." should be --methods.--
Column 5, lines 1-2, "Such apparatus and methods are disclosed and
    claimed herein." should be deleted
Column 5, line 8, --Such apparatus and methods are disclosed and
    claimed herein.-- should be added
Column 5, line 64, "invention invention" should be --invention--
Column 7, line 28, "of the present is" should be --of the present
    invention is--
Column 9, line 33, "has a reached" should be --has reached--
Column 10, line 59, "resistance of" should be --resistance to--
Column 11, line 57, "solubilized+" should be --solubilized--
Column 12, line 34, "so at to" should be --so as to--
Column 12, line 35, "probes 32," should be --probe 32,--
Column 12, line 43, "to add in" should be --to aid in--

Signed and Sealed this

Fourth Day of February 1986

[SEAL]

Attest:

DONALD J. QUIGG

Attesting Officer

Commissioner of Patents and Trademarks